United States Patent [19]

Tao

[11] Patent Number: 4,862,144
[45] Date of Patent: Aug. 29, 1989

[54] MOVEMENT MONITOR

[76] Inventor: Billy S. K. Tao, 6 Jennifer Avenue, Bellevue Heights, South Australia, Australia, 5050

[21] Appl. No.: 176,835

[22] Filed: Apr. 4, 1988

[30] Foreign Application Priority Data

Apr. 21, 1987 [AU] Australia ................. PI1529
Aug. 20, 1987 [AU] Australia ................. PI3861

[51] Int. Cl.$^4$ .................... G08B 23/00; A61B 5/08
[52] U.S. Cl. .................. 340/573; 128/721; 340/665
[58] Field of Search ........... 340/573, 575, 608, 665, 340/666; 128/721–723, 782, 671, 714, 716

[56] References Cited

U.S. PATENT DOCUMENTS

| | | | |
|---|---|---|---|
| 3,325,799 | 6/1967 | Farris | 340/573 |
| 3,875,929 | 4/1975 | Grant | 128/653 |
| 3,903,876 | 9/1975 | Harris | 340/573 X |
| 3,926,177 | 12/1975 | Hardway, Jr. et al. | 128/722 |
| 4,033,332 | 7/1977 | Hardway, Jr. et al. | 128/722 |
| 4,110,741 | 8/1978 | Hubert et al. | 340/573 |
| 4,196,429 | 4/1980 | Davis | 340/669 |
| 4,234,876 | 11/1980 | Murai | 340/573 |
| 4,359,726 | 11/1982 | Lewiner et al. | 340/666 |
| 4,417,572 | 11/1983 | Green | 128/782 X |
| 4,433,693 | 2/1984 | Hochstein | 128/721 |
| 4,494,553 | 1/1985 | Sciarra et al. | 128/721 |
| 4,576,179 | 3/1986 | Manus et al. | 128/671 |
| 4,696,307 | 9/1987 | Montgieux | 128/721 |

FOREIGN PATENT DOCUMENTS

| | | | |
|---|---|---|---|
| 7729443 | 4/1979 | Australia . | |
| 8058956 | 12/1980 | Australia . | |
| 8546089 | 2/1985 | Australia . | |
| 1492875 | 11/1977 | United Kingdom | 128/721 |
| 2081454 | 2/1982 | United Kingdom . | |

Primary Examiner—Swann, III: Glen R.
Assistant Examiner—Thomas J. Mullen, Jr.
Attorney, Agent, or Firm—Kanz, Sherback & Timmons

[57] ABSTRACT

This invention relates to a movement monitor that is suitable for detecting movement, and also provides an alarm should movement that is being monitored cease. The movement monitor is particularly suitable for use with humans or other living organisms where breathing movement is being monitored. In considering the use of the movement monitor on human infants, it is particularly useful for preventing death from Sudden Infant Death Syndrome. The movement monitor comprises a rigid base member for supporting the moving object which is being monitored, and is provided with a reaction means which is secured to the base member and arranged to extend over and be held in contact with the moving object. A transducer is placed between the rigid base member and the moving object such that when movement occurs, the reaction means causes force to be applied to the transducer. The use of the reaction means provides a more positive application of movement force to the transducer thereby providing a greater deal of reliability in detecting movement. The output from the transducer is connected to a circuit means which is arranged to provide an alarm should the output from the transducer sense no movement from the moving object.

31 Claims, 5 Drawing Sheets

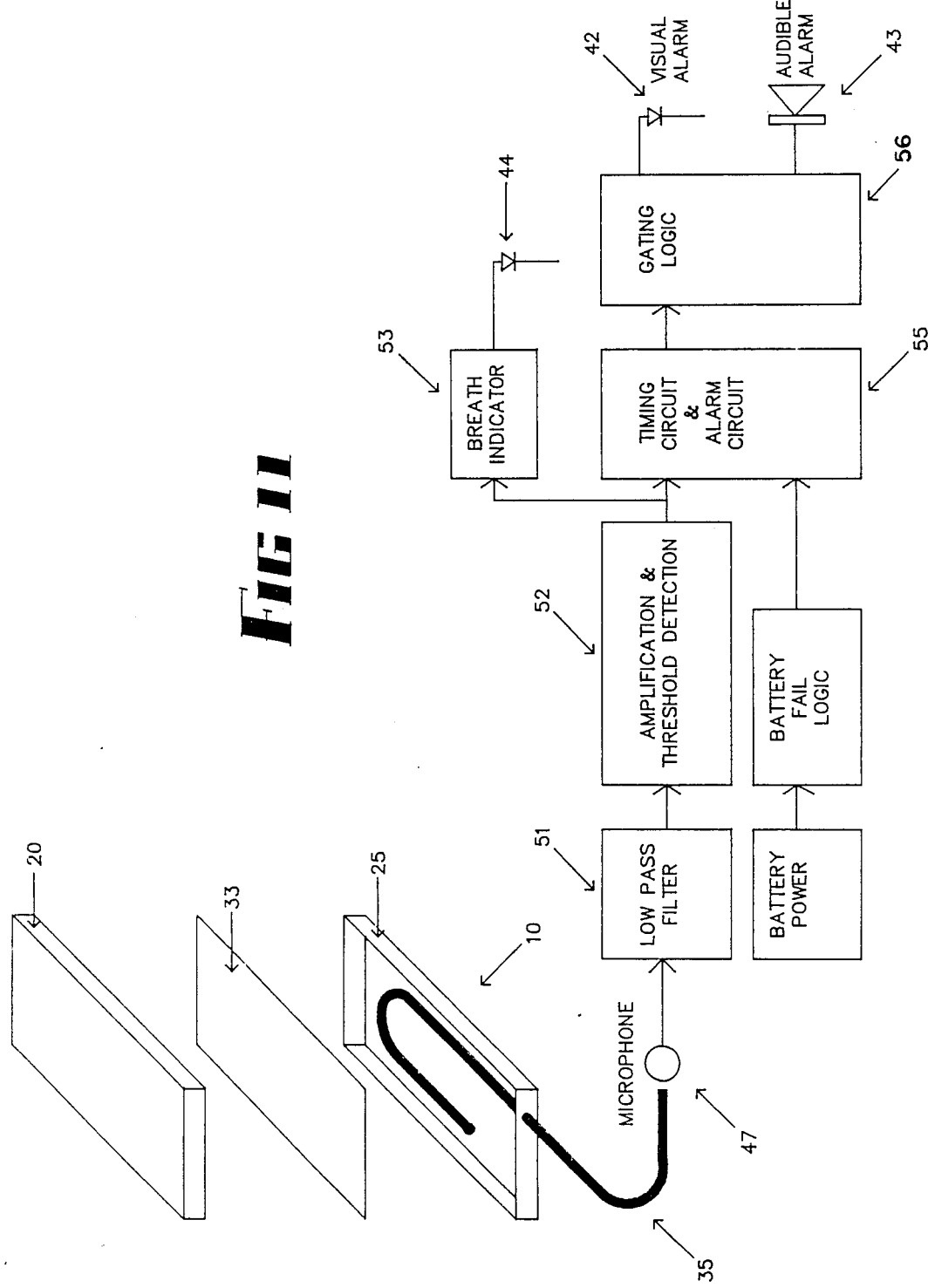

MOVEMENT MONITOR

BACKGROUND OF THE INVENTION

This invention relates to a movement monitor suitable for detecting movement and is useful, although not restricted to, a movement monitor suitable for monitoring a human's or other living organism's breathing movement.

In considering the use of the movement monitor on human infants, it would be particularly useful for preventing Sudden Infant Death Syndrome (S.I.D.S.). S.I.D.S. is now the most common cause of death in industrialised countries among infants aged between one week to one year. The incidence of S.I.D.S. in the countries U.S.A., Great Britain, Canada and Australia are about 1.5 to 2 per thousand infants.

Despite the enormity of the problem, little progress has been made in the actual medical prevention of S.I.D.S. Moreover, because death usually occurs in apparently healthy infants without warning, much of the research work as to the cause of S.I.D.S. has to be done on post-mortem examinations or epidemiological speculations. Alternatively, many studies have been done on near miss S.I.D.S. or "high risk" infants, but unfortunately this group of subjects are not the same as the majority of S.I.D.S. patients who are usually healthy infants with no previous history of apnoea or like illness.

More widespread use of home apnoea or apnoea/-bradycardia monitors may offer one hope of preventing S.I.D.S. It is believed that infants dying from S.I.D.S., may stop breathing for longer than thirty (30) seconds before death or irreversible brain damage, and intervention before this critical time may save their lives. It has also been observed that apnoea could be successfully terminated by stimulation.

Home monitoring programs exist in most countries that have a high incidence of S.I.D.S. However, because of the limitations in monitor design, the cost of running such programs, and the high manpower demand, these programs can only be employed for a limited number of selected "high risk" infants such as siblings from previous S.I.D.S. victims, infants with past history of Apnoea or Cyanosis, and cases of extreme prematurity. However, there is no existing monitoring program that caters for the normal, non high risk infants because of the shortcomings of existing monitoring systems.

At present there are four (4) popular types of monitors available to detect cessation of chest or abdominal movement. They are:

(i) The Graesby Dynamic MR 10 Respirator Monitor,
(ii) The Vickers Apnoea Alarm Mk 3,
(iii) Pressure sensitive pads placed underneath the infants,
(iv) Impedence systems All of the above monitors are expensive and also very complicated to operate. All of the monitors require numerous tubes, conductors or sensors which are either attached to the infant, or to the mattress, from the main electronic monitoring unit. In the case where sensors need to be attached to the infant, problems are caused when the electrode becomes detached or where attachment causes local skin excoriation. Also, operating the monitors requires skill, and a great deal of training is needed before they can be operated accurately. Also, many of the various types of pressure sensitive pads are small, so that the infant may easily roll off the pads, thereby causing false alarms. Generally, such monitors are perceived as being either inaccurate, unreliable or insensitive.

Therefore, it is an object of this invention to provide a movement monitor that overcomes the above-mentioned problems, and provides a simple system for the general monitoring of movement.

It is a further object of this invention to provide a movement monitor that is suitable for use with an infant, simple to use, inexpensive to manufacture, and accurate in determining the breathing cessation.

Whereas problems exist in monitoring infants, it is also an object of this invention to provide a movement monitor suitable for use with adults or other respiring animals. Also, a person skilled in the art will readily recognise other areas where movement detection will be useful, such as providing an alarm when a machine or other moving device stops operating.

BROAD DESCRIPTION OF THE INVENTION

In its broadest form, the invention comprises a base member for supporting a moving object in which movement is being monitored, a transducer arranged to be located between said moving object and said base member, said transducer providing an output signal in response to forces applied thereto, a reaction means secured to the base member and arranged to extend over, and be held in contact with, the moving object such that movement by the moving object causes force to be applied to the transducer and circuit means for monitoring said output signal from the transducer, said circuit means arranged to provide an alarm when said output from the transducer corresponds to no movement from the object.

It will be readily recognised that there are many applications for a movement monitor as described above, but it will be readily seen that the most suitable application would be where the moving object is a human, and in particular an infant in relation to alerting to the occurrence of breathing cessation. It will be also understood that the supporting function performed by the rigid base member in the case of a human would require some form of comfortable or resilient support means which may incorporate or lay over the transducer. The resilient support means may be in the form of a conventional mattress.

The reason for providing a rigid base member is such that the transducer element which is placed between the moving object and the base member, has a sufficiently rigid surface against which the transducer may act. In other words the base should not substantially deflect, so that all movement can be sensed by the transducer. This is particularly the case where either a strain gauge or some pressure sensing device is used. It will be readily recognised that, when a conventional mattress is used, the transducer element would either lay between the mattress and the rigid base member or be incorporated within the mattress. A person skilled in the art will recognise that the term "rigid" may equally apply to some flexible materials, provided they do not substantially deform under the actual applied forces so as to reduce the sensitivity of movement detection.

As previously mentioned, a preferred use for the invention is with an infant human. Therefore the movement referred to is breathing movement while the infant is asleep. However, as previously mentioned, it will be readily recognised that there will be many other applications where the detection of moving cessation is required.

As indicated above, there are many forms of transducers which may be used to sense the movement being monitored. Also, the output signal from the transducer may be in the form of either an electrical signal or some other form of output such as pressure change, or air movement. A person skilled in the art will readily recognise how any of the many various transducers might be used in accordance with the above description of the invention.

In order to improve the accuracy of the movement monitor, a reaction means is provided that offers some restraint to the movement of the moving object. This restraint causes the force resulting from the moving object acting against the reaction means to be directed more positively into the transducer. Therefore, in the broader sense, the reaction means is secured to the base, and is held in contact with the moving object such that force is transmitted to the transducer. In one aspect of the invention, the reaction means may comprise a strap which is secured to either side of the base member, and is positioned such that it extends over and is held in contact with the moving object. In another aspect of the invention, the reaction means may comprise a rigid member that is secured to one side of the base member, and extends upwardly and over the moving object such that the other end of the rigid member extends over and is held in contact with the moving object.

The output from the transducer is monitored by a circuit means, the circuit means being adapted to provide an alarm should movement cease. It will be obvious to a person skilled in the art that there are many various forms of circuit means that will perform the necessary function, and that the circuit means will be varied in accordance with the type of transducer that is used.

With reference to the above, one form of the invention where the moving object is a human may be as follows; a movement monitor comprising a pressure responsive transducer, a surface for supporting a human comprising a resilient mattress having means for communicating pressure changes within the mattress to the pressure responsive transducer, a rigid base member comprising a housing for supporting and containing the mattress such that the upper surface of the mattress, on which the human is supported, is exposed, a reaction means extending over and held in contact with the human on the mattress such that chest or abdominal movements cause a force to be applied to the mattress, and circuit means for monitoring the output from the said transducer, said output resulting from forces applied to the mattress and said circuit means being arranged to sound an alarm when the output from the said transducer corresponds to an alarm situation.

In another form of the invention where the moving object is a human, a mattress is provided that has resilient foam rubber surrounded by a polymeric material, and the pressure responsive transducer comprises a microphone located within or communicating with the internal portion of the mattress, such that the pressure changes within the mattress are monitored by the transducer. Also, the pressure responsive transducer may comprise a pair of microphones wherein a first microphone is measuring the internal pressure changes of the mattress along with outside noise and other extraneous signals, and a second microphone, that is either located within the mattress or adjacent to the mattress, is sealed so as to only be able to respond to noise and extraneous signals, the said signals from the two microphones being processed by the circuit means such that the signal from the second microphone cancels the noise signal from the first microphone. The resulting signal therefore relates only to pressure changes. Also a further microphone, used either in combination with the abovementioned microphones or only with the microphone measuring the internal mattress pressure changes, may be provided such that it measures the ambient pressure changes caused by changing weather conditions, high winds or other momentary changes. The signal from this further microphone is also processed by the circuit such that extraneous ambient pressure changes are cancelled from the signal coming from the microphone measuring the internal mattress pressure changes.

In a further aspect of this invention where the moving object is a human, the pressure responsive transducer may comprise a pressure sensing means located between the mattress and the housing, such pressure sensing means comprises an air-sac communicating with a pressure transducer, the air-sac being resiliently deformable so as to resume its original rest volume when force is removed and capable of registering forces applied to the mattress as pressure changes within the air-sac sensed by the transducer.

As mentioned when the moving object is a human the reaction means may comprise a strap that is positioned and held across the human laying on the mattress, such that breathing movements will result in a downward force being applied to the mattress. Preferably, the strap may be secured to either side of the housing via a sliding support means that allows the longitudinal position of the strap relative to the human to be adjusted.

In order that the invention may be clearly understood and readily carried into effect, preferred embodiments will now be described by way of examples only with reference to the accompanying representations wherein:

FIG. 11 shows a circuit means for use with a microphone installed in a resilient tube.

Figure 1:
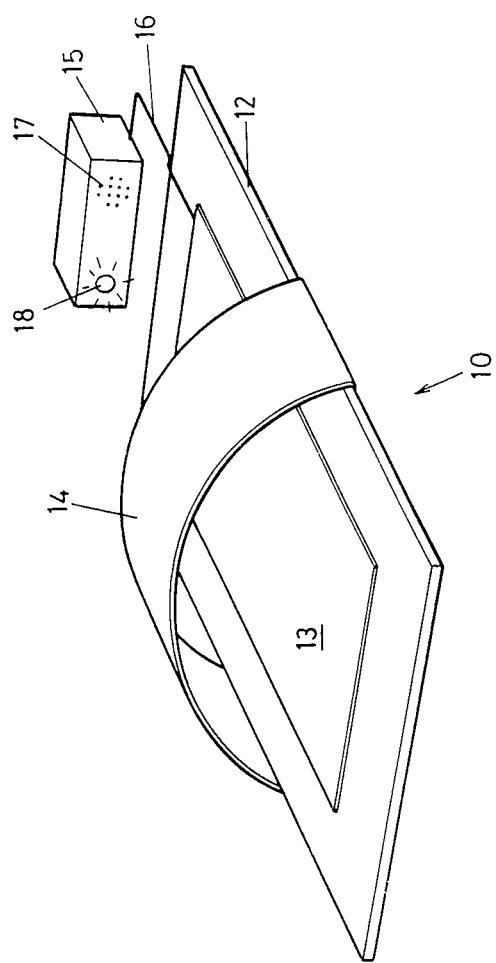
FIG. 1 shows a movement monitor.

In the following embodiments a movement monitor is described in relation to use of an infant human. As shown in FIG. 1, the movement monitor 10 comprises a rigid base member 12, a transducer 13, a reaction means 14, and a circuit means 15. The output from the transducer 13 is fed into the circuit means and, obviously, the type of output from the transducer will vary in accordance with the type of transducer used. The output may be either electrical or pressure related.

The rigid base member 12 may be constructed from any type of substantially rigid material, but in this embodiment it preferably comprises a polymeric material.

In this embodiment, the transducer 13 comprises an air-sac in which the internal pressure changes in the air-sac due to forces applied to the transducer are communicated via the output 16 to the circuit means 15.

The reaction means 14 comprises a fabric strap which is secured at either side of the rigid base member 12. In use, the infant is located between the transducer and the reaction means 14. The reaction means 14 extends over and is held in contact with the infant, such that the breathing movements of the infant are more positively applied to the transducer 13.

The circuit means 15 receives the output from the transducer 16, and while movement is being detected by the transducer 13, the circuit means 15 will remain in the non-alarm state. As soon as a signal ceases to be received from the transducer 13, then the circuit means 15 will provide an alarm in the form of an audio output 17 and a visual signal 18.

Figure 4:
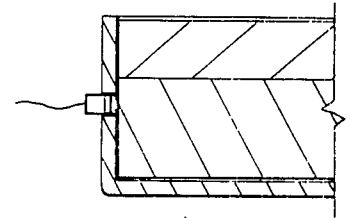
FIG. 4 shows cross-section detail of the microphone mounting to the tray and communication of the mattress internal pressure changes with the microphone.

In a second embodiment where the movement monitor is used with an infant, the surface for supporting the infant comprises a mattress 20 constructed from a series of resilient foam materials and an outer polymeric cover 24 and located in a housing 25. The mattress 20 has a pressure transducer 21 associated with it that comprises a microphone for sensing pressure changes that result from forces applied to the mattress 20. A skilled person will be aware that many microphones, particularly smaller microphones, are provided with a vent behind the sensing surface of the microphone. Obviously this vent hole needs to be sealed, or as shown in FIG. 4, the microphone 21 may be placed within a hole in a side wall of the housing 25, and the mattress 20 may be provided with an aperture that allows internal pressure changes to be sensed by the microphone 21. The mattress 20 may be arranged to tightly fit within the housing 25 such that the contact between the polymeric cover 24 and the housing 25 provide a substantially air-tight seal.

The internal foam material of the mattress 20 comprises a top layer 22 of substantially impervious and resilient material and a lower layer 23 of porous foam material. The top layer 22 preferably comprises material which is stiffer than the bottom layer 23, which results in a larger pressure change for any given applied force. This is due to the substantially enlarged surface area movement resulting from any applied force. The mattress 20 is located within a housing 25 that comprises a tray-like member. The housing 25 is arranged to support and contain the mattress 20 such that only the upper surface which supports the infant is exposed. This also assists in transferring any pressure changes from within the mattress 20 to the pressure transducer 21 arranged in communication with the internal air volume of the mattress 20 by preventing expansion of side and base walls. The housing 25 is preferably manufactured from a rigid plastic such as ABS or polypropylene and is arranged in relation to the mattress 20 such that it provides a snug or tight fit for the mattress 20.

Figure 2:
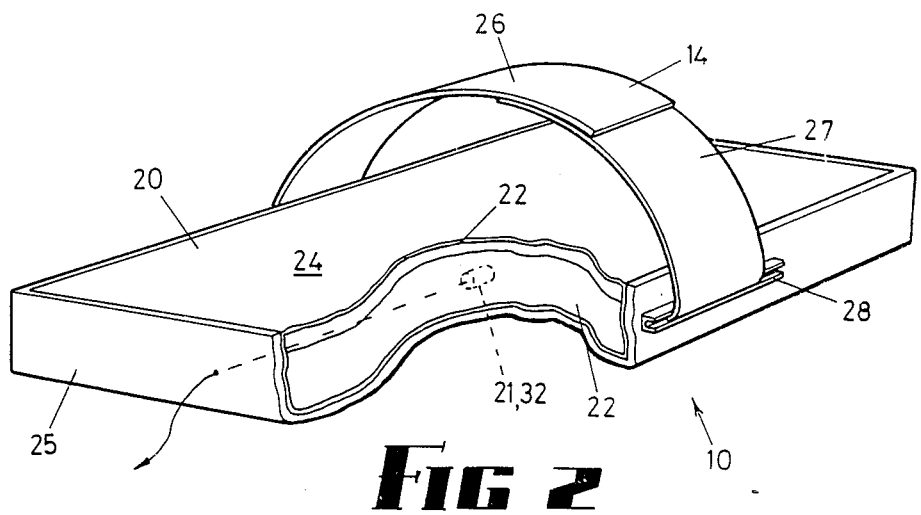
FIG. 2 shows a movement monitor where the rigid base comprises a tray, a mattress is provided in the tray, and the transducer comprises a microphone.
Figure 3:
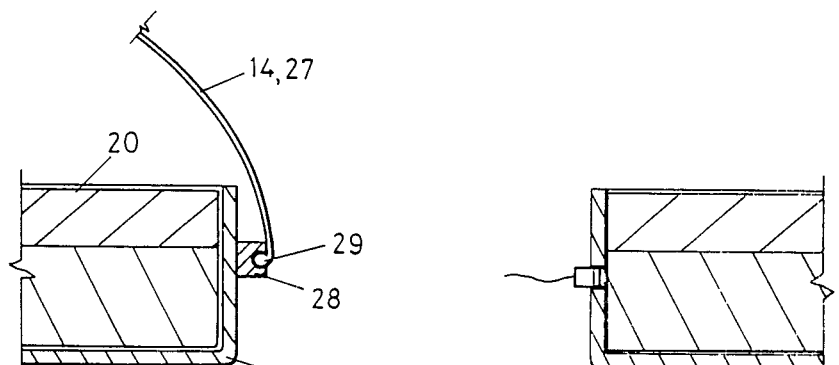
FIG. 3 shows detail of attachment of the reaction means strap to the tray.

The polymeric cover 24 is manufactured from a soft material such as sheet vinyl or sheet polypropylene. The pressure transducer 21 can be either installed within the mattress 20 as shown in FIG. 2 or a vent hole can be provided within the surface of the mattress 20 whereby either the pressure transducer 21 is mounted over the hole as shown in FIG. 4. A tube or other communication means may also be used for transferring the pressure changes to the pressure transducer 21.

The reaction means 14 comprises a material strap which is in two portions 26 and 27. The two portions 26 and 27 of the reaction means 14 can be joined by reusable fastening means similar to the product known under the trade name of VELCRO. The housing 25 is provided with a pair of elongated channels 28 which are located on each side of the housing 25. An end of each of the two portions 26 and 27 of the reaction strap 14 are provided with runners 29 that engage within the channels 28 such that the runners 29 can slide longitudinally while being held captive within the elongate channels 28. This will allow the reaction means 14 to be easily and readily positioned over and held in contact with the chest and abdominal region of the infant on the mattress 20.

As the pressure transducer 21 provides a high sensitivity, it is not necessary to either precisely position the reaction means 14 or to carefully adjust its tension. This will further assist in the ease of locating and fixing of the reaction means 14 and will result in a reliable signal being provided.

Figure 5:
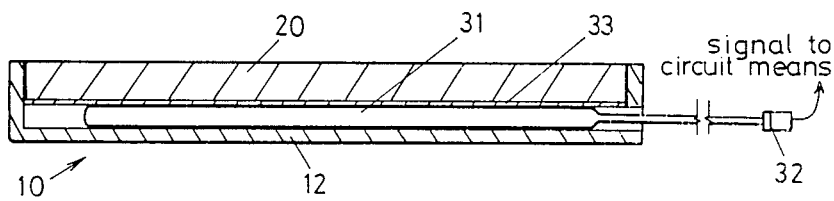
FIG. 5 shows a cross-section through a movement monitor using a transducer that comprises a deformable air-sac.

FIG. 5 shows a third embodiment of the movement monitor 10 in which the transducer 13 comprises a resiliently deformable air-sac 31 wherein the pressure changes within the deformable air-sac 31 are monitored by a pressure transducer 32. The deformable air-sac 31 comprises a means which encapsulates a volume of air and is positional between the mattress 20 and the rigid base member 12. Any force applied to the mattress 20 will cause deformation of the deformable air-sac 31 which in turn will cause pressure changes within the air-sac. These pressure changes will be monitored and detected by the pressure transducer 32. In order to improve reception and detection of the forces by the deformable air-sac 31, a plate 33 is located between the mattress 20 and the deformable air-sac 31. The plate 33 is substantially rigid and causes the force which may be localised on the mattress 20 to be applied over a greater area of the deformable air-sac 31, thereby improving the strength of signal and reliability of receipt of signal from the pressure transducer 32.

As mentioned above, the mattress 20 may comprise a foam filled polymeric cover 24. However, it may also comprise a water filled mattress.

Preferably, the resiliently deformable air-sac 31 may comprise a resilient tube 35 which has a pressure transducer 32 inserted within one end of the tube 35. The other end of the resilient tube 35 is blocked. In this embodiment the pressure transducer 32 comprises a microphone that senses the pressure changes, thereby providing an electrical signal to the circuit means.

Figure 6:
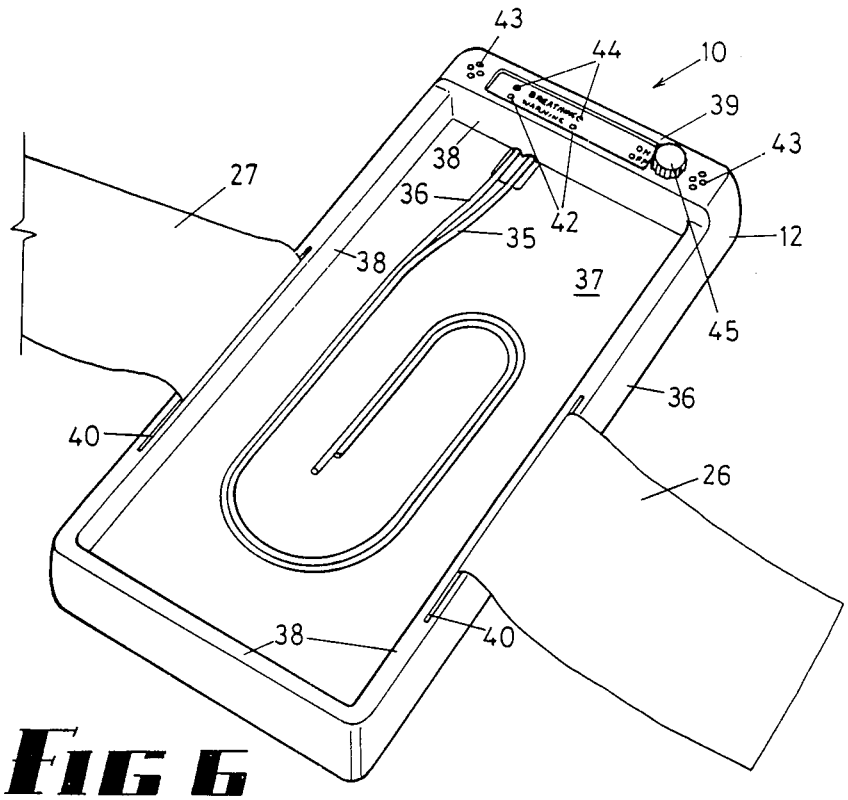
FIG. 6 shows a movement monitor wherein the transducer comprises a pair of resilient tubes.

FIG. 6 shows an illustration of a movement monitor 10 incorporating features of this embodiment. The rigid base member 12 comprises a tray 36 having a rigid base portion 37 surrounded by walls 38. One of the walls 38 is enlarged to provide a chamber 39 in which the circuit means is installed.

In this embodiment a pair of circuit means is provided such that should one of the circuits fail, the remaining circuit will still provide the monitoring function. Therefore, FIG. 6 shows a pair of resilient tubes 35 positioned on the rigid base portion 37 of the tray 36. A plate 33 comprising a rigid sheet of plastic (not illustrated in FIG. 6) is then laid in position over the top of the resilient tubes 35. The mattress 20 then can be positioned over the plate 33, wherein the mattress 20 is held in position by the walls 38.

Although FIG. 6 shows a pair of resilient tubes 35, a single resilient tube (not illustrated) may be used. The single tube would be connected between the pair of pressure transducers, thereby doing away with the need of blocking the ends of the tubes.

In this embodiment the reaction means 14 comprises an elongated strip of material which is positioned underneath the tray 36 with the two portions 26 and 27 of the reaction means 14 retained within slots 40 within the side walls 38 of the tray 36. The two portions 26 and 27 of the reaction means 14 are provided with a releasable fastening means such that the two portions 26 and 27 can be releasably fastened.

The resilient tubes 35 may be simply coiled or looped beneath the mattress 20 such that the tubes 35 extend over as much of the area of the rigid base portion 37 as is possible.

In other embodiments the deformable air-sac 31 instead of comprising resilient tubes 35 may comprise an integral moulding (not illustrated) such that the deformable air-sac 31 is in the form of a mat which is positionable between the rigid base portion 37 and the mattress 20.

As mentioned above, the function of the circuit means 15 is to provide an alarm in relation to the cessation of movement. In the embodiment shown in FIG. 6, the alarm comprises a pair of warning lights 42 and a pair of speakers 43. In addition, a pair of indication lights 44 are provided which give an indication of movement occurring on the mattress. As the downward force is applied to the transducer 13, the indication lights 44 will illuminate thereby providing a ready indication that movement is occurring, even though the movement may not be visually discernible. The operation of the circuit means 15 is controlled by a switch 45.

The circuit means 15 will vary in accordance with the type of transducer that is used, but in the embodiments described in this specification the main transducer used is a microphone which is adapted to act as a pressure transducer 21 and 32.

Figure 7:
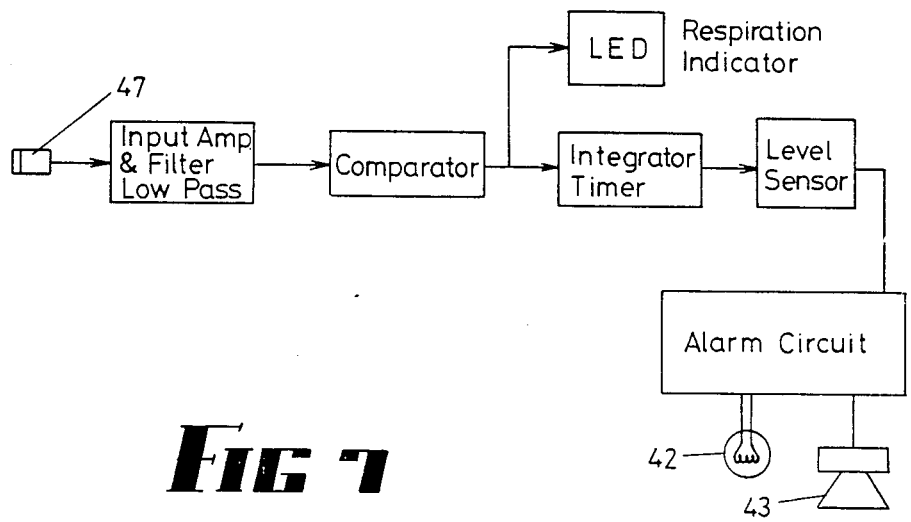
FIG. 7 shows a circuit means for use with a single microphone.

In an aspect of the invention, a circuit means 15 using a single microphone is illustrated in FIG. 7. In this illustration the pressure transducer is a microphone 47 which is positioned either within or in close proximity to the mattress 20 so that any pressure changes within the mattress, which is a substantially sealed unit, will be sensed by the microphone 47. The signal emanating from the microphone 47 is passed through a low filter and an amplifying unit. The function of the low pass filter is to differentiate between normal movement signals, which in the case of a breathing infant, will fall within a specified range of frequencies, and to exclude all other extraneous frequencies. The amplifier serves to increase the signal strength. A comparator circuit conditions the signal to produce a pulse waveform which is synchronous with the breathing cycle. This comparator then drives an L.E.D. indicator and discharges an integrator timing circuit. If the integrator timer is not provided with an input from the comparator, it commences a timing program which will result in an output signal from the integrator time at the end of a specified time. The timing program is interrupted and re-set provided that a signal is regularly received from the comparator. In the case of a breathing infant, the integrator timer is arranged to provide a first signal at between ten (10) to fifteen (15) seconds of elapsed time, at which point the level sensor receives the signal and commences a first stage of alarm. The first stage of alarm in this embodiment comprises intermittent flashing of the warning lights 42 and intermittent sound emissions from the speakers 43. At the end of a further ten (10) to fifteen (15) seconds of receiving no signal from the comparator the integrator timer will produce a further output which is sensed by the level sensor, and the level sensor in turn produces a second stage alarm which comprises continual illumination of the warning lights 42 and continual emission of sound from the speakers 43.

Figure 8:
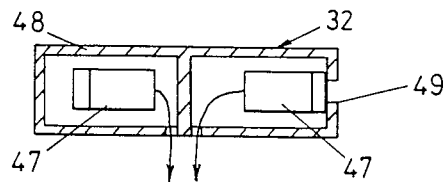
FIG. 8 shows a capsule for use with a pair of microphones.

One difficulty which is encountered in measuring pressure changes within the mattress 20 by using a microphone 47 is that external noises or disturbances, as well as the unwanted noise generated by the microphone 47, are also included in the breathing signal. Although breathing rates are commonly about 0.67 Hz it is possible that extraneous noise may cause a continuous signal that maintains the movement monitor 10 in a non-alarm situation, even though movement may have ceased. In a further aspect of this invention, the circuit means 15 is designed to cancel the extraneous noise signals from the movement signal. As shown in FIG. 8 the pressure transducer 32 comprises a pair of microphones 47 installed within a capsule 48. The capsule 48 is divided into two halves, such that a microphone 47 may be installed within each of the halves. In one of the halves an aperture 49 is provided such that pressure changes can be sensed by the microphone 47 in that half of the capsule 48. The other half of the capsule is fully sealed such that the microphone 47 in that half will not sense pressure changes.

When this pressure transducer 21 is used in the embodiment illustrated in FIG. 2, any extraneous noise not related to pressure changes within the mattress will be sensed by both microphones, and by using a differential amplifier as illustrated in FIG. 8, the difference between the two signals will represent pressure change only, therefore representing only the movement forces which are applied to the mattress 20.

Figure 9:
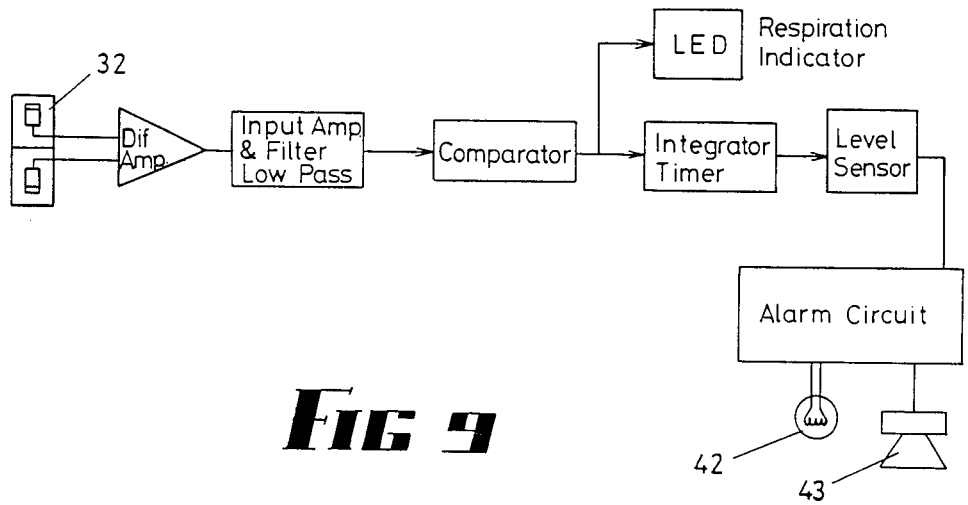
FIG. 9 shows a circuit means for use with a pair of microphones.
Figure 10:
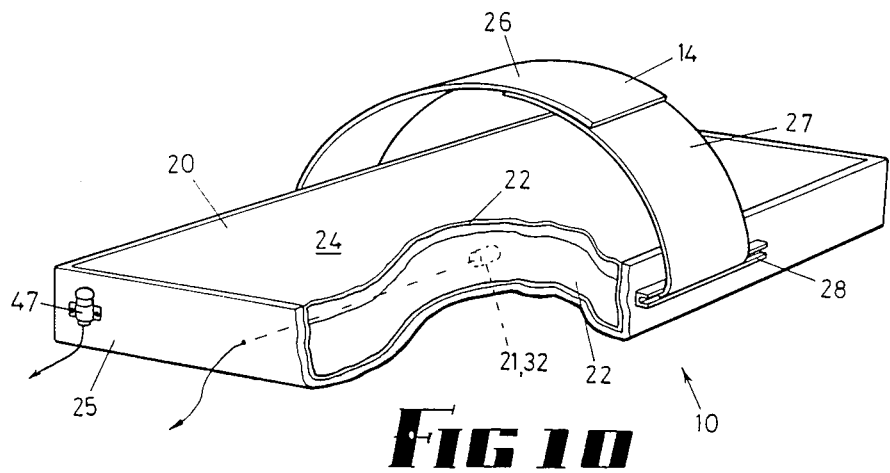
FIG. 10 shows a movement monitor using an externally mounted microphone.

In a further aspect of this invention, the pair of microphones 47 may be installed on the movement monitor 10 as is illustrated in FIG. 10. One of the microphones 47 would be installed within the mattress, or at least in communication with the internal air volume of the mattress 20, sensing pressure changes occurring within the mattress 20, and the second microphone could be located externally of the mattress 20 such that it is measuring external pressure changes and noise elements. The output from both of the microphones 47 may also be fed into a differential amplifier similar to that illustrated in FIG. 9 such that again the pressure change resulting from movement on the mattress 20 may be isolated.

A final circuit means, which is used in the embodiment of the movement monitor 10 as illustrated in FIG. 6, is shown in FIG. 11. The input signal comes from a microphone 47 located within a rubber tube 35. The pressure changes within the rubber tube 35 are sensed by the microphone 47, and the signal from the microphone 47 is conditioned by a low pass filter 51, and is then fed into an amplification and threshold detection circuit 52. An output from the amplification and threshold detection circuit 52 provides on/off switching for an indicator circuit 53 and indicator light 44 and that output exists provided a set threshold of breathing movement is detected.

The output of the amplification and threshold detection circuit 52 is fed into a timing and alarm circuit 55 that will commence operation upon not receiving an output from circuit 52, when the breathing movement does not reach the set threshold. The first timed period is a ten (10) to fifteen (15) seconds such that after ten (10) to fifteen (15) seconds of receiving no output from circuit 52, the timing and alarm circuit 55 operates a gating logic circuit 56. The gating logic circuit 56 then activates the visual alarm 42 that comprises a red light, and also energises the audible alarm which comprises a speaker 43. The gating logic circuit 56 controls the visual alarm and audible alarm such that it gives a half second pulse every three seconds.

Should the movement signal remain low for a further ten (10) to fifteen (5) seconds, the timing and alarm circuit 55 will provide a further output to operate the gating logic circuit 56. The gating logic circuit 56 then permanently energises the visual alarm 42, and permanently drives the audible alarm speaker 43.

The circuitry is arranged such that should the movement recommence after the first alarm has been activated, the circuit means 15 will return to a normal operation mode, but the gating logic circuit 56 will hold the visual alarm 42 in an on position, thereby indicating the activation of an alarm. Should movement cessation be for a period shorter than ten (10) to fifteen (15) seconds, then no alarm will sound.

Should the second alarm be activated, the only means of de-energising the visual and audible alarm 42 and 43 is to attend to the movement monitor 10 and switch off the power to the circuit means 15.

The various circuit means 15 described above are also provided with a battery fail wherein should the battery output level fall below a predetermined safe level, the audible alarm 43 will be energised to provide three (3) second outputs every ten (10) seconds.

Preferably, the various circuit means 15 are provided with separate battery power to the audible alarm, since the operation of the alarm results in a significant drain of battery power. It is intended that the battery fail circuit will sense the battery's power in both the audible alarm and the circuit means.

Preferably, the various circuit means 15 are provided with a backup circuit means wherein the backup is an exact duplicate of the first circuit means, such that monitoring will occur should one of the circuit means fail. Also, the circuit means may be designed with self checking facilities such that an alarm will be produced if a fault occurs within the transducer 13.

In further embodiments, instead of a pressure sensitive transducer 21 being associated within the mattress, it is also intended that the surface for supporting a human may comprise other forms of transducers. Other transducers that may be suitable for use are piezoelectric devices that are mounted either beneath the mattress surface or on top of the mattress surface. A piezoelectric device comprising the film-like piezoelectric material would be most suitable. Also, the surface may comprise a trampoline-like member extended across the tray support wherein strain gauges are positioned between the surface and the connection to the support such that downward movement on the surface results in an output from the strain gauges.

The claims defining the invention are as follows:

I claim:

1. A movement monitor comprising:
    a rigid base member for supporting a moving object in which movement is being monitored,
    a transducer located between said moving object and said base member for detecting movement of said moving object, said transducer providing an output signal in response to forces applied thereto,
    a reaction means secured to the base member and arranged to extend over, and be held in contact with, the moving object such that upward movement by the moving object is restricted by said reaction means and movement by the moving object against said reaction means causes force to be applied to the transducer, and
    circuit means for monitoring said output signal from the transducer, said circuit means arranged to provide an alarm when said output from the transducer corresponds to no movement from the object.

2. A movement monitor according to claim 1 wherein the moving object is a living organism and the monitor is used to monitor the breathing movement of the living organism while asleep wherein the movement monitor further comprises a mattress located between the transducer and the reaction means for support of the living organism.

3. A movement monitor according to claim 1 wherein the moving object is a living organism and the monitor is used to monitor the breathing movement of the living organism while asleep wherein the movement monitor further comprises a mattress having the transducer arranged to be in communication with the internal air volume of the mattress, said mattress positioned on the rigid base member for support of the living organism.

4. A movement monitor according to claim 1 wherein the transducer comprises a mattress having a substantially air tight cover and a pressure transducer arranged in communication with the internal air volume of said mattress such that forces applied to said mattress cause pressure changes which are detected by said pressure transducer, said pressure transducer providing an output proportional to the pressure changes.

5. A movement monitor according to claim 4 wherein the pressure transducer comprises a microphone.

6. A movement monitor according to claim 4 wherein the pressure transducer comprises a pair of microphones with a first microphone in communication with the internal air volume of said mattress and a second microphone sealed such that said first microphone responds to both pressure changes and external noise and said second microphone responds only to external noise, the circuit means receiving both output from said microphones and having circuit elements for removing the external noise component from the output of said first microphone.

7. A movement monitor according to claim 6 wherein said microphones are positioned in a pair of chambers within a capsule, said capsule having a first chamber with an aperture and a second chamber which is sealed.

8. A movement monitor according to claim 4 wherein the pressure transducer comprises a pair of microphones, wherein a first microphone is in communication with the internal air volume of said mattress and a second microphone is located externally of said mattress such that said first microphone responds to both pressure changes and external noise and said second microphone responds to atmospheric pressure changes and external noise, the circuit means receiving both outputs from said microphones and having circuit elements for removing the atmospheric pressure changes and external noise components from the output of said first microphone.

9. A movement monitor in accordance with any of claims 4 to 8 wherein the mattress includes padding comprising a first upper layer of substantially non-porous material and a lower layer of substantially porous material, wherein the upper layer is stiffer than the lower layer.

10. A movement monitor according to claim 1 wherein the transducer comprises a deformable air-sac in combination with a pressure transducer wherein the pressure transducer is in communication with the internal air volume of the deformable air-sac.

11. A movement monitor according to claim 10 wherein said deformable air-sac comprises a resilient tube closed at one end and connected to the pressure transducer at the other end.

12. A movement monitor according to claim 11 wherein a plate is positioned over the resilient tube for transfer of said forces to the resilient tube.

13. A movement monitor according to either claim 10, claim 11 or claim 12 wherein the moving object is a living organism and the monitor is used to monitor the breathing movement of the living organism while asleep wherein the movement monitor further comprises a mattress located between the transducer and the reaction means for support of the living organism.

14. A movement monitor according to claim 13 wherein the mattress comprises a water filled mattress.

15. A movement monitor according to either claim 1 or claim 10 wherein the rigid base member comprises a tray having a rigid base portion surrounded by walls, said transducer located on said rigid base portion within said walls.

16. A movement monitor according to claim 15 wherein a mattress is used which is of such size that it fits tightly within the walls of the said tray.

17. A movement monitor according to claim 16 wherein the tray is further provided with a chamber within which the circuit means is located.

18. A movement monitor according to claim 15 wherein the tray is further provided with a chamber within which the circuit means is located.

19. A movement monitor according to either claim 1 or claim 10 wherein said reaction means comprises a fabric strap attached to either side of said rigid base member.

20. A movement monitor according to claim 19 wherein said fabric strap has two portions releasably fixed to one another for securement over the moving object.

21. A movement monitor according to claim 20 wherein the strap is fixed to the rigid base member at each side by way of a fixture which allows sliding movement of the strap in a longitudinal direction.

22. A movement monitor according to claim 21 wherein the base is provided with a slot on each side of the base such that the said fabric strap extends underneath the rigid base member and protudes at either side through said slots, said fabric strap being movable longitudinally within said slots.

23. A movement monitor according to claim 19 wherein the strap is fixed to the rigid base member at each side by way of a fixture which allows sliding movement of the strap in a longitudinal direction.

24. A movement monitor according to claim 23 wherein the base is provided with a slot on each side of the base such that said fabric strap extends underneath the rigid base member and protrudes at either side through said slots, said fabric strap being movable longitudinally within said slots.

25. A movement monitor according to claim 1 or claim 10 wherein the alarm of said circuit means comprises both a visual alarm and an audible alarm.

26. A movement monitor according to claim 25 wherein the alarm has two stages, the first stage providing intermittent visual and audible alarm, the second stage providing continuous visual and audible alarm.

27. A movement monitor according to claim 26 wherein there is provided an indication light which illuminates upon application of a force to said transducer.

28. A movement monitor according to claim 26 wherein said first stage alarm is actuated after between ten (10) and fifteen (15) seconds of no movement being sensed from the object, and wherein said second stage operates upon a further time period from said first stage of between ten (10) and fifteen (15) seconds.

29. A movement monitor according to claim 28 wherein there is provided an indication light which illuminates upon application of a force to said transducer.

30. A movement monitor according to claim 25 wherein there is provided an indication light which illuminates upon application of a force to said transducer.

31. A movement monitor according to claim 1 or claim 10 wherein said circuit means are powered by batteries.

* * * * *